US008735614B2

(12) United States Patent
Gilbeau et al.

(10) Patent No.: US 8,735,614 B2
(45) Date of Patent: *May 27, 2014

(54) PROCESS FOR THE MANUFACTURE OF 1,2-EPOXY-3-CHLOROPROPANE

(75) Inventors: Patrick Gilbeau, Braine-le-comte (BE); Frederic Gillin, Malonne (BE)

(73) Assignee: Solvay SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/981,320

(22) PCT Filed: Jan. 25, 2012

(86) PCT No.: PCT/EP2012/051149
§ 371 (c)(1),
(2), (4) Date: Jul. 24, 2013

(87) PCT Pub. No.: WO2012/101176
PCT Pub. Date: Aug. 2, 2012

(65) Prior Publication Data
US 2013/0303793 A1    Nov. 14, 2013

(30) Foreign Application Priority Data

Jan. 27, 2011 (EP) .................................. 11152407

(51) Int. Cl.
C07D 301/12 (2006.01)
(52) U.S. Cl.
USPC ........................................................ 549/531
(58) Field of Classification Search
USPC ........................................................ 549/531
See application file for complete search history.

(56) References Cited

U.S. PATENT DOCUMENTS

| | | | |
|---|---|---|---|
| 4,833,260 A | 5/1989 | Neri et al. |
| 5,374,747 A | 12/1994 | Saxton et al. |
| 6,169,050 B1 | 1/2001 | Catinat et al. |
| 6,288,248 B1 | 9/2001 | Strebelle et al. |
| 6,350,888 B1 | 2/2002 | Strebelle et al. |
| 6,380,407 B1 | 4/2002 | Catinat et al. |
| 6,429,322 B1 | 8/2002 | Catinat et al. |
| 6,465,382 B1 | 10/2002 | Strebelle et al. |
| 6,590,112 B1 | 7/2003 | Catinat et al. |
| 6,603,027 B1 | 8/2003 | Catinat et al. |
| 6,677,467 B2 | 1/2004 | Balthasart |
| 6,699,812 B2 | 3/2004 | Strebelle et al. |
| 6,720,435 B2 | 4/2004 | Balthasart et al. |
| 6,723,861 B2 | 4/2004 | Balthasart |
| 6,815,552 B2 | 11/2004 | Strebelle et al. |
| 6,838,571 B2 | 1/2005 | Balthasart |
| 7,205,419 B2 | 4/2007 | Strebelle et al. |
| 7,320,779 B2 | 1/2008 | Strebelle et al. |
| 7,323,578 B2 | 1/2008 | Catinat et al. |
| 7,834,202 B2 | 11/2010 | Strebelle et al. |
| 7,863,211 B2 | 1/2011 | Strebelle et al. |
| 8,058,459 B2 | 11/2011 | Catinat et al. |
| 2006/0041150 A1* | 2/2006 | Catinat et al. ................ 549/531 |
| 2008/0132718 A1 | 6/2008 | Strebelle et al. |
| 2010/0113808 A1 | 5/2010 | Liebens et al. |
| 2010/0331557 A1 | 12/2010 | Strebelle et al. |

FOREIGN PATENT DOCUMENTS

| | | |
|---|---|---|
| CN | 1769277 A | 5/2006 |
| CN | 101480623 A | 7/2009 |
| CN | 101486690 A | 7/2009 |
| CN | 101481364 B | 12/2010 |
| EP | 1243333 A2 | 9/2002 |
| JP | 4059769 A | 2/1992 |
| WO | WO 96/03362 A1 | 2/1996 |
| WO | WO 99/24164 A1 | 5/1999 |
| WO | WO 99/28029 A1 | 6/1999 |
| WO | WO 99/28035 A1 | 6/1999 |
| WO | WO 00/07722 A1 | 2/2000 |
| WO | WO 01/57012 A1 | 8/2001 |
| WO | WO 02/00634 A1 | 1/2002 |
| WO | WO 2004043941 A1 | 5/2004 |
| WO | WO 2004048353 A1 | 6/2004 |
| WO | WO 2008122503 A1 | 10/2008 |
| WO | WO 2012101175 A1 | 8/2012 |

OTHER PUBLICATIONS

Clerici, M.G., et al., "Epoxidation of Lower Olefins with Hydrogen Peroxide and Titanium Silicate" 1993, Journal of Catalysis, vol. 140, pp. 71-83, Elsevier Science Publishers B.V. Amsterdam; 13 pgs.
Notari, B., "Titanium Silicalite: A New Selective Oxidation Catalyst", 1991, Structure—Activity and Selectivity Relationships in Heterogeneous Catalysis, R.K. Grasselli and A.W. Sleight Editors, Elsevier Science Publishers, B.V., Amsterdam, pp. 243-256; 14 pgs.
Van Der Poel, A.J.H.P., et al—"Parameters affecting the synthesis of titanium silicalite 1", 1992, Applied Catalysis A: General, 92, vol. 92, pp. 93-111, Elsevier Science Publishers B.V., Amsterdam; 19 pgs.
Thangaraj, A., et al, "Studies on synthesis of titanium silicalite, TS-1", 1992, Zeolites, vol. 12, November/December, Butterworth-Heinemann, pp. 943-950; 8 pgs.
Kumar, R., et al; "Chemo-Selective Oxidation of Organic Halides Catalyzed By TS-1 Under Solvent-Free Triphase Conditions Using Dilute H2O2", 1999, Proceedings of the 12th International Zeolite Conference, 1999 Materials Research Society, pp. 1227-1232; 6 pgs.
U.S. Appl. No. 09/294,363, filed Apr. 20, 1999, Catinat et al.
U.S. Appl. No. 09/199,570, filed Nov. 25, 1998, Strebelle et al.
U.S. Appl. No. 09/508,731, filed May 26, 2000, Strebelle et al.
U.S. Appl. No. 09/554,113, filed Jul. 12, 2000, Strebelle et al.
U.S. Appl. No. 09/555,454, filed May 31, 2000, Catinat et al.
U.S. Appl. No. 10/054,859, filed Jan. 25, 2002, Strebelle et al.
U.S. Appl. No. 10/790,023, filed Mar. 2, 2004, Strebelle et al.
U.S. Appl. No. 09/646,788, filed Sep. 22, 2000, Catinat et al.
U.S. Appl. No. 09/646,787, filed Sep. 22, 2000, Catinat et al.
U.S. Appl. No. 10/940,992, filed Sep. 15, 2004, Strebelle et al.
U.S. Appl. No. 11/682,904, filed Mar. 7, 2007, Strebelle et al.
U.S. Appl. No. 10/297,927, filed Dec. 19, 2002, Balthasart.

(Continued)

Primary Examiner — Taylor Victor Oh
(74) Attorney, Agent, or Firm — Xuping Fu

(57) ABSTRACT

Process for the manufacture of 1,2-epoxy-3-chloropropane by reaction between allyl chloride and hydrogen peroxide in the presence of a solid catalyst and in the possible presence of at least one solvent in an epoxidation medium comprising at least two liquid phases under the conditions of reaction, wherein the catalyst exhibits an external surface to volume ratio lower than to $2.4 \cdot 10^4$ $m^{-1}$.

19 Claims, No Drawings

(56) References Cited

OTHER PUBLICATIONS

U.S. Appl. No. 10/311,308, filed Dec. 27, 2002, Balthasart.
U.S. Appl. No. 10/650,730, filed Aug. 29, 2003, Balthasart.
U.S. Appl. No. 10/311,305, filed Dec. 27, 2002, Balthasart et al.
U.S. Appl. No. 10/476,879, filed Nov. 13, 2003, Catinat et al.
U.S. Appl. No. 10/534,299, filed May 9, 2005, Strebelle et al.
U.S. Appl. No. 12/880,210, filed Sep. 13, 2010, Strebelle et al.
U.S. Appl. No. 10/534,502, filed Sep. 19, 2005, Catinat et al.
U.S. Appl. No. 12/593,958, filed Sep. 30, 2009, Liebens et al.
U.S. Appl. No. 13/981,340, filed Jul. 24, 2013, Gilbeau et al.

* cited by examiner

PROCESS FOR THE MANUFACTURE OF 1,2-EPOXY-3-CHLOROPROPANE

The present application is a U.S. national stage entry under 35 U.S.C. §371 of International Application No. PCT/EP2012/051149 filed Jan. 25, 2012, which claims priority benefit to European patent application no EP 11152407.0 filed on Jan. 27, 2011, the whole content of this application being incorporated herein by reference for all purposes.

Should the disclosure of any of the patents, patent applications, and publications that are incorporated herein by reference conflict with the present specification to the extent that it might render a term unclear, the present specification shall take precedence.

The invention relates to a process for the manufacture of 1,2-epoxy-3-chloropropane by reaction between allyl chloride and hydrogen peroxide.

It is known to manufacture 1,2-epoxy-3-chloropropane (or epichlorohydrin) by epoxidation of allyl chloride by means of hydrogen peroxide in the presence of methanol as solvent and in the presence of a catalyst comprising TS-1, as disclosed in M. G. Clerici et al., Journal of Catalysis, 140, 71-83 (1993). The use of methanol as solvent is required to obtain a good activity of the catalyst and a good selectivity to epichlorohydrin. The use of large quantities of the solvent however presents the drawbacks related to the need for its separation, recovery and recycling, which add to the complexity of the process.

Derwent Abstract of Chinese patent application 101481364 describes the manufacture of epichlorohydrin by epoxidation of allyl chloride by means of hydrogen peroxide in the presence of a minimum amount of methanol as solvent and in the presence of a titanium-silicon molecular sieve catalyst. The catalyst is a powder. The catalyst is separated by filtration, resuspended by the solvent and recycled to the reaction. The use of a powder catalyst exhibits the disadvantage that the catalyst recovery operation and recycling make the process more complicated.

The present invention is targeted at overcoming the previous disadvantages by providing a novel process in which the drawbacks linked to the solvent and catalyst recovery are greatly reduced without, however, reducing substantially the activity of the catalyst (or the degree of conversion of the reactants, or the rate of the epoxidation reaction) and the catalyst lifetime, and without substantially increasing the formation of by products.

The invention consequently relates to a process for the manufacture of 1,2-epoxy-3-chloropropane by reaction between allyl chloride and hydrogen peroxide in the presence of a solid catalyst and in the possible presence of at least one solvent in an epoxidation medium comprising at least two liquid phases under the conditions of reaction, wherein the catalyst exhibits an external surface to volume ratio lower than or equal to $2.4\ 10^4\ m^{-1}$.

Combining the use of a catalyst exhibiting an external surface to volume ratio lower than or equal to $2.4\ 10^4\ m^{-1}$ with a two liquid phase reaction mixture presents at least one of the following advantages:

Provision of a catalyst which has a shape such that it is easy to separate from the reaction mixture, and facilitate the regeneration of the catalyst;

Reduction of alcoholysis byproducts in case where an alcohol is used as a solvent;

Enhancement of the epichlorohydrin purity by reduction of the contamination of the final product by the solvent and by-products formed by the solvent;

Reduction and possibly removal of the operations of separation of solvent;

Reduction of the volume of a solvent recycling loop and possibly removal of the loop;

Easiness to carry out the overall process continuously;

Possibility to use catalytic fixed-bed or fluid-bed reactors with admissible pressure drop;

Reduction of the overall cost of the process by reducing the number of process down-stream steps.

Those advantages can be obtained with almost no impact on the reaction rate and on the epichlorohydrin selectivity. This is surprising since, without willing to be tied by any theory, combining biphasic epoxidation conditions with a catalyst exhibiting the claimed surface/volume ratio feature, one would expect a very low reaction rate due to the cumulative negative effects of liquid phase segregation for the reactants (mass transfer problem) and diffusion problems within the catalyst particles. Such conditions would in addition request higher reaction times for acceptable productivity of epichlorohydrin with a negative impact on the epichlorohydrin selectivity due to secondary subsequent reactions of epichlorohydrin solvolysis.

The volume of the catalyst is understood to mean the geometric volume of the bed of the macroscopic catalyst. The bed can be of any type like for instance, fixed bed, fluid bed, moving bed, entrained bed or circulating bed. Fixed bed and moving bed are preferred, the fixed bed being most preferred. The volume of the catalyst bed is understood to mean the volume of the catalyst in operation during the process.

The "external surface" of the catalyst is understood to mean the surface of the catalyst particles constituting the catalyst bed. The external surface does not include the surface of the catalyst particles due to a possible macro-, meso- and/or microporosity of the catalyst particles. Such a porosity is generally such that the equivalent pore diameter is lower than 5 μm, often lower than 2 μm and frequently lower than 1 μm. Catalyst particles are intended to mean solid element of catalyst such as powders, extrudates, pellets, etc., honeycomb structures, catalytic micro-reactors and structured packings like Katapack®, Melapack®, etc. The catalyst can be a bulk catalyst or a supported catalyst.

The volume can be calculated from the geometrical dimensions of the catalyst bed.

The external surface can be calculated from the average geometric outer dimensions of the catalyst particles, using classical surface and volume formulas. If no shape can be defined for the catalyst particles, they are considered as spheres and the geometric outer dimension is the diameter of the equivalent sphere.

In the process according to the invention, the catalyst particles can exhibit any form. The catalyst particle is generally in a form selected from the group consisting of rings, beads, pellets, tablets, extrudates, granules, crushed, saddled, flakes, honeycomb structures, impregnated structured packings and any mixture thereof.

When the catalyst is in the form of beads, the beads are considered as spheres and the geometric outer dimension is the diameter of the equivalent sphere.

When the catalyst is in the form of cylindrical particles (e.g. pellets, extrudates), the catalyst particles are considered as cylinders and the geometrical outer dimensions are the average particle diameter and the average particle length. The average can be geometric, arithmetic or logarithmic. The arithmetic average is for instance particularly convenient.

When the catalyst particles do not have simple geometrical form like for instance, crushed, flakes, saddles, extrudates of various forms (stars, etc.), they are considered as spheres and the geometrical outer dimensions is the diameter of the equivalent sphere.

When the catalyst particles are in the form of cylindrical rings, the catalyst particles are considered as hollow cylinders and the geometrical dimensions are the average diameters (internal and external) of the cylinders, and the average length of the cylinders.

When the catalyst is the form of a honeycomb structure with cylindrical channels, the geometrical dimensions are the average length and diameter of the channels.

Those are only a few examples on how the geometrical outer dimensions of the catalyst particles needed for calculating the external surface to volume ratio of the catalyst can be defined. The man of ordinary skill in the art will easily understand how to obtain those dimensions for any catalyst form, including the forms not disclosed hereabove.

The value of the characteristical outer dimensions of catalyst particles can be obtained by any means, for instance, by visual or microscopic measurements on individual catalyst particles followed by averaging the measure on a sufficiently large number of particles (e.g. more than 100) to be statistically reliable or from particle size distribution via sifting, sedimentation (natural or forced) methods or light scattering methods for instance.

In the process according to the invention, the catalyst exhibits an external surface to volume ratio which is often lower than or equal to $2.0 \times 10^4$ m−1, frequently lower than or equal to $1.5 \times 10^4$ m−1, specifically lower than or equal to $1.0 \times 10^4$ m−1, more often lower than or equal to $0.75 \times 10^4$ m−1, more frequently lower than or equal to $0.6 \times 10^4$ m−1, particularly lower than or equal to $0.5 \times 10^4$ m−1, more particularly lower than or equal to $0.3 \times 10^4$ m−1 and in many cases lower than or equal to $0.1 \times 10^4$ m−1.

This ratio is generally higher than or equal to $10\,m^{-1}$, often higher than to $20\,m^{-1}$, frequently higher than or equal to $50\,m^{-1}$, specifically higher than or equal to $75\,m^{-1}$, particularly higher than or equal to $100\,m^{-1}$ and in many cases higher than or equal to $150\,m^{-1}$.

In the process according to the invention, the catalyst is preferably provided in the form selected from the group consisting of beads, extrudates, honeycomb structures and any mixture thereof.

In a first preferred aspect of the process according to the invention, the catalyst is advantageously provided in the form of beads (spherical particles) obtained by any known method. A method which is particularly well suited is that disclosed in International Application WO 99/24164 from Solvay (Société Anonyme). The catalyst particles exhibit a mean diameter of greater than 0.10 mm, more preferably of greater than or equal to 0.25 mm and most preferably of greater than or equal to 0.4 mm. That mean diameter is usually less than or equal to 5 mm, preferably less than or equal to 2 mm, more preferably less than or equal to 1 mm and most preferably of less than or equal to 0.8 mm. The catalyst particles generally exhibit a specific surface of greater than or equal to 1 $m^2/g$ and less than or equal to 900 $m^2/g$ (determined according to the nitrogen adsorption method), a bulk density of between 0.1 and 1.0 g/ml, a pore volume of between 0.25 and 2.5 ml/g and a distribution of the diameters of the pores with a maximum of between 15 and 2000 Å.

In a second preferred aspect of the process according to the invention, the catalyst is advantageously provided in the form of non-spherical particles obtained, for example, as extrudates obtained by extrusion as disclosed in International Application WO 99/28029 from Solvay (Société Anonyme). The shape of the extruded granules is arbitrary. They may be solid or hollow. They may be of round or rectangular cross-section, or alternatively a different cross-section with a greater external surface area. Cylindrical shapes are preferred. When they are of cylindrical shape, the extruded granules advantageously have a mean diameter of at least 0.5 mm, preferably of at least 1 mm. The mean diameter is usually at most 5 mm, particularly at most 2 mm. The cylindrical shapes have usually a mean length of at least 1 mm, particularly of at least 2 mm. Mean lengths of at most 8 mm are current, those of at most 4 mm give good results. The cylindrical shapes having a mean diameter of from 0.5 to 5 mm, preferably from 1 to 2 mm, and a mean length of from 1 to 8 mm, preferably from 2 to 4 mm are suitable.

In a third preferred aspect of the process according to the invention, the catalyst is advantageously provided in the form of a honeycomb structure. "Honeycomb" structure is understood to denote a shape composed of components with a cellular structure, whatever the shape of the cells. The honeycomb is generally provided in the form of a cartridge comprising a number of cell per inch ($cpi^2$) higher than or equal to 10, preferably higher than or equal to 50 and more preferably higher than or equal to 70. This number of cells per $inch^2$ ($cpi^2$) is usually lower than or equal to 1200, preferably lower than or equal to 900, more preferably lower than or equal to 800, yet more preferably lower than or equal 450, and still more preferably lower than or equal to 400.

In the process according to the invention, the catalyst preferably comprises a zeolite.

Zeolite is understood to denote a solid comprising silica which exhibits a microporous crystalline structure. The zeolite is advantageously devoid of aluminium. The zeolite comprises titanium. The zeolite according to the invention is preferably a zeolite in which several silicon atoms have been replaced by titanium atoms.

Good results have been obtained with zeolites of titanium silicalite type. The latter advantageously exhibit a crystalline structure of ZSM-5, ZSM-11 or MCM-41 type or of beta type. They preferably exhibit an infrared absorption band at approximately 950-960 $cm^{-1}$. Those corresponding to the formula $xTiO_2(1-x)SiO_2$ in which x is from 0.0001 to 0.5, preferably from 0.001 to 0.05, are highly effective. Materials of this type, known under the name of TS-1, exhibit a microporous crystalline zeolite structure analogous to that of the zeolite ZSM-5. The properties and the main applications of these compounds are known (B. Notari, Structure-Activity and Selectivity Relationship in Heterogeneous Catalysis, R. K. Grasselli and A. W. Sleight Editors, Elsevier, 1991, p. 243-256). Their synthesis has been studied in particular by A. Van der Poel and J. Van Hooff (Applied Catalysis A, 1992, Volume 92, pages 93-111) and by Thangaraj et al. (Zeolites, 12 (1992), 943-950).

The zeolite content in the catalyst according to the invention, expressed as percentage by weight of zeolite in the catalyst, is generally greater than or equal to 1% and less than or equal to 60%. The zeolite content is preferably greater than or equal to 5% and less than or equal to 40%.

In the third preferred aspect according to the invention, the catalyst comprises a titanium containing zeolite deposited by impregnation on a honeycomb-shaped support as described above. The honeycomb-shaped support is advantageously composed of an inert material which withstands the regeneration conditions and on which it is possible to make the zeolite adhere by means of a binder. Silicas are highly suitable as support. It can relate, for example, to silicas combined with other magnesium or aluminium oxides and their mixtures. The support is preferably cordierite or mullite. A particular preference is shown for cordierite because it results in better adhesion of the zeolite to the support.

In the process according to the invention, the solvent optionally used is a solvent which dissolves epichlorohydrin well and usually in which water is sparingly soluble. Preferably, a solvent which also dissolves the starting allyl chloride well can be used.

The solvent is preferably an organic solvent. The solvent can be selected from the group consisting of an alcohol, a saturated aliphatic hydrocarbon possibly containing at least one halogen atom, an unsaturated aliphatic hydrocarbon possibly containing at least one halogen atom, an aromatic hydrocarbon possibly containing at least one of a halogen atom, a nitrogen atom and an alkyl group, and any mixtures of at least two of them.

The alcohol, often contains from 1 to 5 carbon atoms and comprise only one —OH group. Examples which may be mentioned are methanol, ethanol, n-propanol, isopropanol, n-butanol, isobutanol, s-butanol, t-butanol and pentanol. Usually, the alcohol is methanol or t-butanol. Methanol is particularly preferred.

When the solvent is an alcohol, more specifically an alcohol fully miscible with water, the content of this alcohol in the epoxidation medium is such that the epoxidation medium comprises at least two liquid phases under the conditions of the epoxidation reaction.

The optionally halogenated unsaturated hydrocarbons comprises preferably from 3 to 20 carbon atoms.

The aromatic hydrocarbon possibly containing at least one of a halogen atom, a nitrogen atom and an alkyl group, comprises preferably from 6 to 12 carbon atoms.

The solvent is preferably selected from the group consisting of methanol, n-decane, n-tridecane, 1,2,3-trichloropropane, decahydronaphtalene, o-dichlorobenzene, m-dichlorobenzene, p-dichlorobenzene, o-xylene, m-xylene, p-xylene, 1,3,5-trimethylbenzene, decaline, o-chlorotoluene, m-chlorotoluene, p-chlorotoluene, nitrobenzene and mixtures thereof. The solvent is often methanol.

In the process according to the invention, the term "epoxidation medium" in which the epoxidation reaction of the process according to the invention takes place is understood to mean a medium comprising at least two liquid phases, comprising allyl chloride, hydrogen peroxide, if appropriate the solvent, the 1,2-epoxy-3-chloropropane formed and optionally byproducts, water and a solid phase comprising the catalyst.

In the process according to the invention, the epoxidation medium comprises at least two liquid phases, at least one first liquid phase, essentially aqueous, comprising the hydrogen peroxide and at least a portion of the solvent, if appropriate, and at least one second liquid phase, essentially organic, comprising allyl chloride, the 1,2-epoxy-3-chloropropane formed, optionally byproducts and at least one other portion of the solvent, if appropriate. The first liquid phase may comprise organic compounds other than the solvent. The second liquid phase may comprise water. The epoxidation medium may be devoid of solvent.

In the process according to the invention, it may furthermore prove to be advantageous to maintain the pH of the epoxidation medium during the epoxidation at a selected value, as disclosed in International Application WO 2004/048353. The latter corresponds, during a measurement carried out at ambient temperature with a Metrohm® 6.0239.100 electrode (electrolyte 3M KCl) on a withdrawn sample of the epoxidation medium, to values of greater than or equal to 1.5, in particular of greater than or equal to 3, more particularly of greater than or equal to 3.2. The pH is advantageously maintained at a value of less than or equal to 5, more especially of less than or equal to 4.8, values of less than or equal to 4.5 and particularly of less than 4 giving good results. When the pH is maintained at a value of greater than or equal to 3 and of less than or equal to 4.5, the advantage is observed, in comparison with a process carried out at natural pH without control of the pH, that the selectivity is higher without a reduction in the activity.

The pH can be controlled by addition of a base or of a mixture of a salt and of its conjugate base or acid. The base can be chosen from water-soluble bases. They can be strong bases or weak bases. Mention may be made, as examples, of an alkali metal or alkaline earth metal hydroxide, carbonate or acetate. Sodium hydroxide is preferred. The pH is measured as described above with vigorous stirring of the two liquid phases, so as to obtain a constant and reproducible pH measurement throughout the stirred medium.

In the process according to the invention, it may furthermore prove to be advantageous to employ an allyl chloride purified so that it comprises less than 2000 ppm of 1,5-hexadiene, as disclosed in International Application WO 2004/043941. This is because it has been found that the use of purified allyl chloride makes it possible to increase the duration of use of the catalyst (and thus to reduce the frequency with which the catalyst has to be removed from the epoxidation medium in order to be replaced or to be regenerated) while retaining a high activity and a high selectivity.

The purified allyl chloride can be obtained by any appropriate known means, for example by chlorination, as disclosed in International Application WO 96/03362. The purification can also be carried out by distillation.

The purified allyl chloride generally comprises an amount of 1,5-hexadiene of less than 1000 ppm by weight and preferably of less than or equal to 500 ppm by weight; values of less than or equal to 400 ppm by weight and in particular of less than or equal to 300 ppm are the most advantageous. The amount of 1,5-hexadiene present in the purified allyl chloride is usually greater than or equal to 1 ppm by weight, generally greater than or equal to 10 ppm by weight.

In the process according to the invention, the hydrogen peroxide is advantageously employed in the form of an aqueous solution. The aqueous solution generally comprises at least 10% by weight of hydrogen peroxide, in particular at least 20% by weight. It usually comprises at most 70% by weight of hydrogen peroxide, in particular at most 50% by weight.

Generally, the molar ratio of the amount of allyl chloride employed to the amount of hydrogen peroxide employed is greater than or equal to 0.1, in particular greater than or equal to 0.5 and preferably greater than or equal to 1. This ratio is usually less than or equal to 100, more especially less than or equal to 50, generally less than or equal to 25. In a particularly advantageous alternative form of the process according to the invention, use is made of an excess of allyl chloride so that the molar ratio of the amount of allyl chloride employed to the amount of hydrogen peroxide employed is greater than or equal to 1, in particular greater than or equal to 2, very particularly greater than or equal to 4. In this advantageous alternative form, the ratio is generally less than or equal to 10, more especially less than or equal to 8 and usually less than or equal to 7. A ratio of approximately 5 is particularly well suited. The use of an excess of allyl chloride in this alternative form makes it possible to obtain an even greater increase in the selectivity and, in combination with the purified allyl chloride, makes it possible to also obtain a reduction in the deactivation of the catalyst.

The catalyst can be present in the process according to the invention in the form of a bed. It can be a stationary bed or a fluid bed. A stationary bed is preferred. Such kind of bed is advantageously used when the catalyst particles are in the form of rings, beads, pellets, tablets, extrudates, granules, crushed flakes, a honeycomb structure or mixtures thereof.

Stationary beds made of beads, extrudates or a honeycomb structure are preferred.

The epoxidation reaction of the process according to the invention can be carried out in any type of appropriate reactor. It can, for example, be a single-pass bed. It can also be a reactor of loop type comprising recirculation of the epoxidation medium, preferably without recirculation of the catalyst.

The temperature at which the epoxidation reaction can be carried out is generally greater than or equal to 0° C., in particular greater than or equal to 35° C., more particularly greater than or equal to 45° C. and preferably greater than or equal to 55° C. The temperature is usually less than or equal to 120° C., more especially less than or equal to 100° C., generally less than or equal to 80° C., temperatures of less than or equal to 65° C. giving highly satisfactory results. When the temperature is from 45 to 80° C., the advantage is observed, in comparison with a lower temperature, for example of approximately 35° C., that the rate of deactivation of the catalyst is reduced.

The process of the invention can be carried out at any pressure at least equal to the vapour pressure of the constituents of the epoxidation medium.

The process according to the invention can be carried out continuously or batchwise, preferably continuously.

When carried out continuously, the process according to the invention usually comprises feeding continuously a reaction zone comprising the catalyst with at least allyl chloride, hydrogen peroxide and possibly at least one solvent. The feed rate is such that the total liquid linear velocity is generally higher than or equal to 0.01 m/s, often higher than or equal to 0.02 m/s, frequently higher than or equal to 0.03 m/s, in many cases higher than or equal to 0.1 m/s and specifically higher than or equal to 0.2 m/s. This feed rate of the liquid is such that the total liquid linear velocity is generally lower than or equal to 1 m/s, often lower than or equal to 0.8 m/s, frequently lower than or equal to 0.6 m/s and specifically lower than or equal to 0.5 m/s. Under such conditions of total liquid linear velocity, the pressure drop across the reaction zone is usually lower than or equal to 25 kPa/m, frequently lower than or equal to 20 kPa/m, often lower than or equal to 15 kPa/m, more frequently lower than or equal to 12 kPa/m, often lower than or equal to 10 kPa/m, more specifically lower than 5 kPa/m. This pressure drop across the reaction zone is usually higher than or equal to 0.02 kPa/m, frequently higher than or equal to 0.05 kPa/m, often higher than or equal to 0.08 kPa/m, more frequently higher than or equal to 0.1 kPa/m, more often higher than or equal to 0.4 kPa/m, specifically higher than or equal to 0.5 kPa/m and more specifically higher than or equal to 0.8 kPa/m.

The total liquid linear velocity is understood to mean the linear velocity of the total liquid feed of the reaction zone containing the catalyst.

The total linear velocity is obtained by dividing the flow of the total liquid feed of the reaction zone containing the catalyst by the section of said zone.

The total liquid feed can be measured by any means like for instance via orifices, venturies, nozzles, rotameters, Pitot tubes, calorimetrics, turbine, vortex, electromagnetic, Doppler, ultrasonic, thermal or Coriolis flow meters.

The section of the said reaction zone is understood to mean the average section along the length of the said reaction zone. Said reaction zone can be horizontal or vertical.

The pressure drop across the reaction zone containing the catalyst is understood to mean the dynamic pressure drop including the pressure drop corresponding to the fluid devices connected to the zone.

The pressure drop can be measured by any means like for instance differential pressure (Dp) cells, manometers such as U tube manometer, cup manometer, bourdon manometer, Piranni manometer, ionisation manometer, membrane manometer, piezo electric manometer, and any combination thereof Preferred means are selected from the group consisting of Dp cells, U tube manometer, bourdon manometer, membrane manometer, piezo electric manometer, and any combination thereof. More preferred means are selected from the group consisting of Dp cells, membrane manometer, piezo electric manometer, and any combination thereof.

The process according to the invention makes it possible to obtain selectivities which are generally greater than or equal to 90 mol % for epichlorohydrin, calculated as in the examples described later, in particular greater than or equal to 95%. The selectivity is usually less than or equal to 99.5%, more especially less than or equal to 99%.

The examples below are intended to illustrate the invention without, however, limiting it.

EXAMPLES

The tests were carried out in a plant composed essentially of a tubular reactor, jacketed under pressure, in a liquid-solid fixed bed (honeycomb structure, 3 superimposed Corning C 119 cartridges with characteristics for one cartridge: diameter: 2.6 cm, height: 10 cm, 400 channels per square inch, square channels of 1×1 mm, 68.8 square inch per cubic inch), with a recirculation loop. The loop comprises in particular a reflux condenser, at atmospheric pressure, positioned directly at the outlet of the reactor (condensation of the allyl chloride). The overall volume of the plant was approximately 310 ml.

The temperature of the reactor was regulated using a cryothermostat.

The pressure in the reactor was regulated at 1.0 bar using a pneumatic valve.

The epoxidation medium was reduced in pressure from its exit from the reactor and the liquid-gas mixture resulting therefrom was cooled by passing into a jacketed glass coil. The temperature set point of the cryothermostat was fixed at −20° C.

The liquid phase was divided into two streams at the outlet of the condenser:
  the liquid outflow, the flow rate of which corresponded to that of the reactant feeds,
  and a second greater outflow, which formed the recirculation shuttle. The $H_2O_2$, allyl chloride (ALC) and possibly methanol (MeOH) feeds were added to this recirculation stream.

Movement towards the reactor was provided using a membrane pump. The recirculation flow rate was measured using a flow meter and was adjusted to 600 l/h. The total liquid linear velocity was of 0.33 m/s. Before entering the reactor, the liquid passed through a preheater. The pressure drop has been estimated to be lower than 7 kPa/m. The estimation was made following the method and data presented by G Germain, C Chandellier and C Blarel at the $10^{th}$ Journée de l'hydrodynamique Nantes 7-9 Mar. 2005.

Use was made, in these tests, of 16 g of a catalyst provided in the form of a honeycomb-structure made of 3 superimposed Corning C119 cartridges with a TS-1 zeolite deposited on the surface of the honeycomb cells composed of Ti silicalite. The cartridges have been prepared according to process as disclosed International application WO 1999/28035 of Solvay (Société Anonyme). The external surface to volume ratio of the catalyst was estimated to be less than 2800 m$^{-1}$ on the basis of the external surface to volume ratio of the bare Corning C cartridge.

A 35 weight % $H_2O_2$ has been used with a flow rate of 75 ml/h. The feed flow rates for allyl chloride and possibly methanol have been adjusted to obtain an epoxidation medium comprising two liquid phases for the ALC/$H_2O_2$ and MeOH/(MeOH+$H_2O_2$) ratio given in Table 1.

The degree of conversion (DC) of the $H_2O_2$ was calculated from the inlet and outlet flow rates of the $H_2O_2$, the latter being determined using the results of an iodometric assay of the residual $H_2O_2$ in the overflow liquid:

DC(%)=100×($H_2O_2$ employed in mol/h−unconverted $H_2O_2$ in mol/h)/$H_2O_2$ employed in mol/h with unconverted $H_2O_2$=concentration of $H_2O_2$ in the overflow in mol/kg x overflow flow rate in kg/h.

The term "C3 formed" is understood to mean epichlorohydrin (EPI) and the various byproducts resulting from the opening of the oxirane ring, namely 1-chloro-3-methoxy-2-propanol (recorded as 1Cl3OMe2Pol), 1-chloro-2-methoxy-3-propanol (recorded as 1Cl2OMe3Pol), 3-chloro-1,3-propanediol (recorded as MCG) and 1,3-dichloro-2-propanol (recorded as 1,3DCPol).

The EPI/C3 formed selectivity can thus be calculated, from the chromatogram obtained by vapour-phase chromatography of the liquid outflow, using the expression:

EPI/C3f selectivity (%)=100×EPI$_{formed}$ in mol/h/Σ (EPI+1Cl3OMe2Pol+1Cl2OMe3Pol+MCG+1, 3DCPol)$_{formed}$ in mol/h.

Examples 1 to 5 (According to the Invention)

The conditions and results of the tests are presented in Table 1 hereafter.

TABLE 1

| Example | ALC/$H_2O_2$ (mol/mol) | MeOH/(MeOH + $H_2O_2$) (wt %) | T (° C.) | DC (%) | EPI/C3f selectivity (mol %) |
|---|---|---|---|---|---|
| 1 | 1.43 | 21 | 25 | 60 | 96.9 |
| 2 | 1.97 | 9 | 35 | 67 | 94.9 |
| 3 | 2.06 | 33 | 35 | 76 | 95.0 |
| 4 | 4.06 | 21 | 45 | 90 | 92.3 |
| 5 | 1.76 | 34 | 45 | 81 | 90.7 |

The invention claimed is:

1. A process for the manufacture of 1,2-epoxy-3-chloropropane comprising a reaction between allyl chloride and hydrogen peroxide in the presence of a solid catalyst and in the optional presence of at least one solvent in an epoxidation medium comprising at least two liquid phases under the conditions of reaction, wherein the catalyst exhibits an external surface to volume ratio lower than to 2.4×10$^4$ m$^{-1}$, wherein the catalyst comprises a zeolite.

2. The process according to claim 1, wherein the catalyst exhibits an external surface to volume ratio lower than or equal to 1.0×10$^4$ m$^{-1}$.

3. The process according to claim 1, wherein the solvent is selected from the group consisting of an alcohol, a saturated aliphatic hydrocarbon optionally having at least one halogen atom, an unsaturated aliphatic hydrocarbon, optionally having at least one halogen atom, an aromatic hydrocarbon optionally having at least one of a halogen atom, a nitrogen atom, an alkyl group, and any mixtures of at least two thereof.

4. The process according to claim 3, wherein the solvent is selected from the group consisting of methanol, n-decane, n-tridecane, 1,2, 3-trichloropropane, decahydronaphtalene, o-dichlorobenzene, m-dichlorobenzene, p-dichlorobenzene, o-xylene, m-xylene, p-xylene, 1,3,5-trimethylbenzene, decaline, o-chlorotoluene, m-chlorotoluene, p-chlorotoluene, nitrobenzene, and mixtures thereof.

5. The process according to claim 4, wherein the solvent is methanol.

6. The process according to claim 1, wherein the epoxidation medium is devoid of solvent.

7. The process according to claim 1, wherein the catalyst is in a form selected from the group consisting of rings, beads, pellets, tablets, extrudates, granules, saddled, crushed, flakes, honeycomb structures, impregnated structured packings, and any mixture thereof.

8. The process according to claim 7, wherein the catalyst is in the form selected from the group consisting of beads, extrudates, honeycomb structures, and any mixture thereof.

9. The process according to claim 8, wherein the catalyst is in the form of honeycomb structures.

10. The process according to claim 1, being carried out continuously.

11. The process according to claim 10, comprising feeding continuously a reaction zone comprising the catalyst with at least said allyl chloride, said hydrogen peroxide and optionally at least one solvent, at a total liquid linear velocity higher than or equal to 0.01 m/s and lower than or equal to 1 m/s, and wherein the pressure drop across the reaction zone is lower than 25 kPa/m.

12. The process according to claim 1, wherein the pH of the reaction medium is maintained at a value from 1.5 to 4.5, and wherein the allyl chloride employed comprises less than 2000 ppm of 1,5-hexadiene.

13. The process according to claim 1, wherein the reaction is carried out at a temperature from 45 to 80° C.

14. The process according to claim 1, wherein the amounts of said allyl chloride and said hydrogen peroxide employed are such that the molar ratio of said allyl chloride to said hydrogen peroxide is from 1 to 7.

15. The process according to claim 1, wherein the zeolite comprises titanium, and wherein the zeolite exhibits a crystalline structure of ZSM-5, ZSM-11, MCM-41, or beta.

16. The process according to claim 15, wherein the zeolite is TS-1.

17. The process according to claim 1, wherein the catalyst is present in the form of a stationary bed.

18. The process according to claim 17, wherein the catalyst is present in the form of a stationary bed made of beads, extrudates, or a honeycomb structure.

19. The process according to claim 1, wherein the catalyst is present in the form of a fluid bed.

* * * * *